US012773381B2

(12) United States Patent
Stebbins et al.

(10) Patent No.: US 12,773,381 B2
(45) Date of Patent: Oct. 27, 2026

(54) COSMETIC COMPOSITION COMPRISING THIOPYRIDINONE COMPOUNDS, REDUCING AGENT AND ARGININE

(71) Applicant: L'Oreal, Clark, NJ (US)

(72) Inventors: Nicholas David Stebbins, Clark, NJ (US); Rebecca Chen, Princeton, NJ (US)

(73) Assignee: L'Oréal, Paris (FR)

( * ) Notice: Subject to any disclaimer, the term of this patent is extended or adjusted under 35 U.S.C. 154(b) by 121 days.

(21) Appl. No.: 18/392,567

(22) Filed: Dec. 21, 2023

(65) Prior Publication Data

US 2025/0205131 A1 Jun. 26, 2025

(51) Int. Cl.

*A61K 8/49* (2006.01)
*A61K 8/23* (2006.01)
*A61K 8/44* (2006.01)
*A61Q 19/02* (2006.01)

(52) U.S. Cl.

CPC .............. *A61K 8/4933* (2013.01); *A61K 8/23* (2013.01); *A61K 8/44* (2013.01); *A61Q 19/02* (2013.01); *A61K 2800/52* (2013.01)

(58) Field of Classification Search

CPC .......... A61K 8/4933; A61K 8/23; A61K 8/44; A61K 2800/52; A61Q 19/02

See application file for complete search history.

(56) References Cited

U.S. PATENT DOCUMENTS

| | | | | |
|---|---|---|---|---|
| 4,792,443 | A | 12/1988 | Filomeno | |
| 2013/0315847 | A1* | 11/2013 | Marat .................... | A61Q 19/02 424/59 |

FOREIGN PATENT DOCUMENTS

| | | | |
|---|---|---|---|
| FR | 3138036 | A1 | 1/2024 |
| JP | 2006076890 | A | 3/2006 |
| WO | 2012080075 | A1 | 6/2012 |
| WO | 2017102349 | A1 | 6/2017 |
| WO | 2023248935 | A1 | 12/2023 |

OTHER PUBLICATIONS

French Search Report and Written Opinion in FR2406588, mailed Jun. 20, 2024, 13 pages.
Macleman, E. "Sodium Sulfite," The Dermatology Review, Nov. 18, 2022, 8 pages.

* cited by examiner

*Primary Examiner* — Jessica Worsham
(74) *Attorney, Agent, or Firm* — The Marbury Law Group, PLLC

(57) ABSTRACT

The present invention relates to a composition, preferably a cosmetic composition comprising at least one thiopyridinone compound of formula (I) or formula (I'), with at least one reducing agent of formula (II) and arginine. The composition of the present invention brightens or depigments a keratin material, preferably skin. The present invention provides a composition including thiopyridinone compound of formula (I) or formula (I') with increased stability of the thiopyridinone compound of formula (I) or formula (I') over exposure to light.

20 Claims, No Drawings

COSMETIC COMPOSITION COMPRISING THIOPYRIDINONE COMPOUNDS, REDUCING AGENT AND ARGININE

FIELD OF INVENTION

The present invention relates to stabilization of thiopyridinone compounds and a cosmetic composition comprising the thiopyridinone compound. The present invention also relates to cosmetic compositions for whitening and depigmentation of a keratin material, the skin.

BACKGROUND OF INVENTION

Many people develop dark coloured spots or patches on their skin, especially on their faces and hands, over the periods of their lives. These dark spots or marks are due to the presence of high concentration of melanin in the keratinocytes at the surface of the skin.

For the treatment of these pigmentation spots there is a requirement of harmless topical depigmenting substances with a good efficacy, which can also provide skin brightening effect. Some organic compounds such as arbutin, niacinamide and kojic acid are known as skin depigmenting agents.

It is known that certain thiopyridinone compounds exhibit good depigmenting activity, even at low concentration, for example those mentioned in WO2012/080075 and WO2017/102349. The thiopyridinone compound can show strong depigmenting or brightening effects by reducing the production of melanin. There is nevertheless a need to develop a cosmetic composition comprising thiopyridinone compound with increased stability to impart skin brightening and whitening effects.

SUMMARY OF THE INVENTION

The inventors surprisingly discovered that the combination of thiopyridinone compound(s) of formula (I) or (I'), arginine and reducing agent(s) improves the stability, and preferably the photostability of the compound of formula (I) or (I') in the composition. In an aspect of the present invention, there is provided a composition, preferably a cosmetic composition, comprising:

i) at least one compound selected from a compound of formula (I) below, its tautomer of formula (I') below; salts, solvates, hydrates, optical isomers, racemates, or mixtures thereof:

Formula (I)

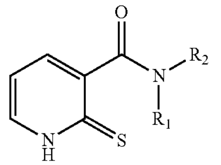

Formula (I')

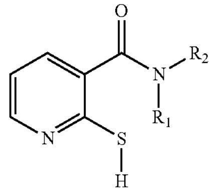

wherein, $R_1$ denotes a radical chosen from:

a) a hydrogen atom;

b) a saturated linear $C_1$-$C_{10}$ or branched $C_3$-$C_{10}$ alkyl group optionally substituted with one or more groups, which may be identical or different, chosen from:

i) —O—$R_3$;

ii) —S—$R_3$;

$R_2$ denotes a radical chosen from:

a) a hydrogen atom;

b) a saturated linear $C_1$-$C_{12}$ or branched $C_3$-$C_{12}$ or cyclic $C_3$-$C_8$ hydrocarbonated group, optionally substituted with one or more groups, which may be identical or different, chosen from:

i) —O—$R_3$;

ii) —S—$R_3$;

iii) —C(O)—O—$R_3$;

iv) a $C_5$-$C_{12}$ aryl group optionally substituted with one or more hydroxyls and/or with one or more $C_1$-$C_8$ alkoxy radicals, and c) a $C_5$-$C_{12}$ aryl group optionally substituted with one or more hydroxyls and/or with one or more $C_1$-$C_8$alkoxy radicals;

$R_3$ denotes a radical chosen from:

a) a hydrogen atom, and b) a saturated linear $C_1$-$C_{10}$ or branched $C_3$-$C_{10}$ alkyl group;

ii) at least one reducing agent of formula (II) its mesomeric forms, and its solvates such as hydrates (II)

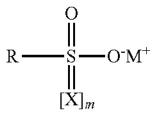

wherein,

X represents a heteroatom selected from oxygen or sulfur, preferably oxygen;

m is 0 or 1;

$M^+$ is a cation, preferably selected from alkali metal, alkaline earth metal or ammonium, more preferably selected from an alkali metal such as sodium or potassium;

R represents a group selected from:

i) —OH, ii) —O-$M'^+$ with $M'^+$ as previously defined for $M^+$,

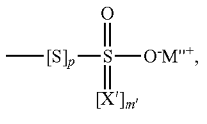

iii) wherein, p is an integer inclusively selected between 0 and 4, preferably 0, 1, 2, and more preferably 0 or 2;

m' is 0 or 1, preferably 1;

X' is as defined for X, preferably X' represents an oxygen atom; and $M''^+$ is as previously defined for $M^+$, and $M^+$, $M'^+$, $M''^+$ are identical or different, preferably identical;

and iii) arginine.

In another aspect of the present invention, there is provided a method of treating a keratin material, the method comprising: applying a composition comprising:

i) at least one compound selected from a compound of formula (I) below, its tautomer of formula (I') below; salts, solvates, hydrates, optical isomers, racemates, or mixtures thereof:

Formula (I)

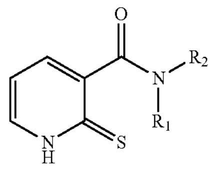

Formula (I')

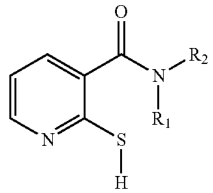

wherein, $R_1$ denotes a radical chosen from:

a) a hydrogen atom; and b) a saturated linear $C_1$-$C_{10}$ or branched $C_3$-$C_{10}$ alkyl group optionally substituted with one or more groups, which may be identical or different, chosen from:

i) —O—$R_3$; and ii) —S—$R_3$;

$R_2$ denotes a radical chosen from:

a) a hydrogen atom;

b) a saturated linear $C_1$-$C_{12}$ or branched $C_3$-$C_{12}$ or cyclic $C_3$-$C_8$ hydrocarbonated group, optionally substituted with one or more groups, which may be identical or different, chosen from:

i) —O—$R_3$;

ii) —S—$R_3$;

iii) —C(O)—O—$R_3$;

iv) a $C_5$-$C_{12}$ aryl group optionally substituted with one or more hydroxyls and/or with one or more $C_1$-$C_8$ alkoxy radicals, and c) a $C_5$-$C_{12}$ aryl group optionally substituted with one or more hydroxyls and/or with one or more $C_1$-$C_8$alkoxy radicals;

$R_3$ denotes a radical chosen from:

a) a hydrogen atom, and b) a saturated linear $C_1$-$C_{10}$ or branched $C_3$-$C_{10}$ alkyl group;

ii) at least one reducing agent of formula (II) its mesomeric forms, and its solvates such as hydrates (II)

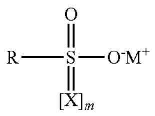

wherein,

X represents a heteroatom selected from oxygen or sulfur, preferably oxygen;

m is 0 or 1;

$M^+$ is a cation, preferably selected from alkali metal, alkaline earth metal or ammonium, more preferably selected from an alkali metal such as sodium or potassium;

R represents a group selected from:

i) —OH, ii) —O-$M'^+$ with $M'^+$ as previously defined for $M^+$, iii)

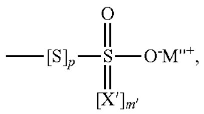

wherein, p is an integer inclusively selected between 0 and 4, preferably 0, 1, 2, and more preferably 0 or 2;

m' is 0 or 1, preferably 1;

X' is as defined for X, preferably X' represents an oxygen atom; and $M''^+$ is as previously defined for $M^+$, and $M^+$, $M'^+$, $M''^+$ are identical or different, preferably identical;

and iii) arginine, on the keratin material, preferably skin.

In another aspect of the present invention, there is provided a use of the composition comprising:

i) at least one compound selected from a compound of Formula (I) below, its tautomer of formula (I') below; salts, solvates, hydrates, optical isomers, racemates, or mixtures thereof:

Formula (I)

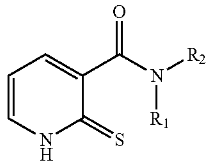

Formula (I')

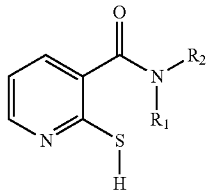

wherein, $R_1$ denotes a radical chosen from:

a) a hydrogen atom;

b) a saturated linear $C_1$-$C_{10}$ or branched $C_3$-$C_{10}$ alkyl group optionally substituted with one or more groups, which may be identical or different, chosen from:

i) —O—$R_3$; and ii) —S—$R_3$;

$R_2$ denotes a radical chosen from:

a) a hydrogen atom;

b) a saturated linear $C_1$-$C_{12}$ or branched $C_3$-$C_{12}$ or cyclic $C_3$-$C_8$ hydrocarbonated group, optionally substituted with one or more groups, which may be identical or different, chosen from:

i) —O—$R_3$;

ii) —S—$R_3$;

iii) —C(O)—O—$R_3$;

iv) a $C_5$-$C_{12}$ aryl group optionally substituted with one or more hydroxyls and/or with one or more $C_1$-$C_8$ alkoxy radicals, and c) a $C_5$-$C_{12}$ aryl group optionally substituted with one or more hydroxyls and/or with one or more $C_1$-$C_8$ alkoxy radicals;

$R_3$ denotes a radical chosen from:

a) a hydrogen atom, and b) a saturated linear $C_1$-$C_{10}$ or branched $C_3$-$C_{10}$ alkyl group;

ii) at least one reducing agent of formula (II) its mesomeric forms, and its solvates such as hydrates (II)

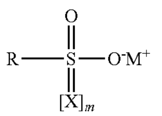

wherein,

X represents a heteroatom selected from oxygen or sulfur, preferably oxygen;

m is 0 or 1;

$M^+$ is a cation, preferably selected from alkali metal, alkaline earth metal or ammonium, more preferably selected from an alkali metal such as sodium or potassium;

R represents a group selected from:

i) —OH, ii) —O-$M'^+$ with $M'^+$ as previously defined for $M^+$, iii)

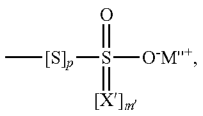

wherein, p is an integer inclusively selected between 0 and 4, preferably 0, 1, 2, and more preferably 0 or 2;

m' is 0 or 1, preferably 1;

X' is as defined for X, preferably X' represents an oxygen atom; and $M''^+$ is as previously defined for $M^+$, and $M^+$, $M'^+$, $M''^+$ are identical or different, preferably identical; and iii) arginine, for brightening or depigmenting a keratin material, preferably skin.

In another aspect of the present invention, there is provided a use of combination of (i) at least one reducing agent of formula (II) its mesomeric forms, and its solvates such as hydrates (II)

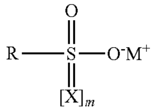

wherein,

X represents a heteroatom selected from oxygen or sulfur, preferably oxygen;

m is 0 or 1;

$M^+$ is a cation, preferably selected from alkali metal, alkaline earth metal or ammonium, more preferably selected from an alkali metal such as sodium or potassium;

R represents a group selected from:

i) —OH, ii) —O-$M'^+$ with $M'^+$ as previously defined for $M^+$, iii)

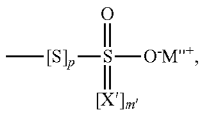

wherein, p is an integer inclusively selected between 0 and 4, preferably 0, 1, 2, and more preferably 0 or 2;

m' is 0 or 1, preferably 1;

X' is as defined for X, preferably X' represents an oxygen atom; and $M''^+$ is as previously defined for $M^+$, and $M^+$, $M'^+$, $M''^+$ are identical or different, preferably identical, and (ii) arginine, in a composition comprising at least one compound selected from compounds of formula (I), its tautomer of formula (I'), salts, optical isomers, racemates, solvates, hydrates, or mixtures thereof:

Formula (I)

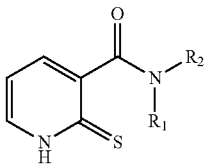

Formula (I')

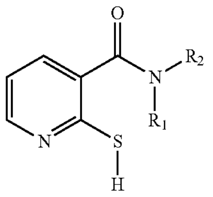

wherein in formulae (I) and (I'):

$R_1$ denotes a radical chosen from:

a) a hydrogen atom;

b) a saturated linear $C_1$-$C_{10}$ or branched $C_3$-$C_{10}$ alkyl group optionally substituted with one or more groups, which may be identical or different, chosen from:

i) —O—$R_3$; and ii) —S—$R_3$;

$R_2$ denotes a radical chosen from:

a) a hydrogen atom;

b) a saturated hydrocarbonated group linear $C_1$-$C_{12}$ or branched $C_3$-$C_{12}$ or cyclic $C_3$-$C_8$, optionally substituted with one or more groups, which may be identical or different, chosen from:

i) —O—$R_3$;

ii) —S—$R_3$;

iii) —C(O)—O—$R_3$;

iv) a $C_5$-$C_{12}$ aryl group optionally substituted with one or more hydroxyls and/or with one or more $C_1$-$C_8$ alkoxy radicals;

c) a $C_5$-$C_{12}$ aryl group optionally substituted with one or more hydroxyls and/or with one or more $C_1$-$C_8$ alkoxy radicals; and $R_3$ denotes a radical chosen from:

a) a hydrogen atom;

b) a saturated linear $C_1$-$C_{10}$ or branched $C_3$-$C_{10}$ alkyl group, to stabilize the compound of formula (I), its tautomer of formula (I'), salts, solvates, hydrates, optical isomers, racemates, or mixtures thereof, in the composition.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

The term "at least one" is used to mean one or more and thus includes individual components as well as mixtures/combinations.

Throughout this specification, unless the context requires otherwise the word "comprise", and variations such as, "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The term "INCI" is an abbreviation of International Nomenclature of Cosmetic Ingredients, which is a system of names provided by the International Nomenclature Committee of the Personal Care Products Council to describe personal care ingredients.

All percentages, parts and ratios are based upon the total weight of the compositions of the present disclosure unless otherwise indicated. Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight percentage range of about 0.01% to 10%, should be interpreted to include not only the explicitly recited limits of about 0.01% to about 10%, but also to include sub-ranges, such as 0.02% to 0.05%, 1% to 10% and so forth, as well as individual amounts, including fractional amounts, within the specified ranges, such as 1.5%, 5.3% and 9.25%, for example.

For the purpose of the present disclosure, unless otherwise indicated:

a) a "saturated linear $C_1$-$C_{12}$ or branched $C_3$-$C_{12}$" hydrocarbonated group is equivalent to a "linear ($C_1$-$C_{12}$) alkyl or branched ($C_3$-$C_{12}$)alkyl group" which correspond to a saturated linear $C_1$-$C_{12}$ or branched $C_3$-$C_{12}$ hydrocarbon based group, and preferably a linear $C_1$-$C_{10}$ or branched $C_3$-$C_{10}$ hydrocarbon based group, and more preferably a linear $C_1$-$C_6$ or branched $C_3$-$C_6$ hydrocarbon-based group; Preferentially, the linear or branched groups may be chosen from methyl, ethyl, propyl, isopropyl, butyl, isobutyl and tert-butyl, pentyl, hexyl, heptyl, octyl, nonyl and decyl. More preferentially, the saturated linear or branched alkyl groups may be chosen from methyl, ethyl, propyl, isopropyl, butyl, isobutyl and tert-butyl, pentyl, hexyl, heptyl and octyl, such as methyl, ethyl, n-pentyl, n-nonyl, isobutyl;

b) a saturated "cyclic $C_3$-$C_8$" hydrocarbonated group is a mono or bicyclic cycloalkyl group containing 3 to 8 carbon atoms especially is a monocyclic cycloalkyl group having $C_5$ to $C_7$ atoms, such as cyclohexyl group;

c) an "alkoxy radical" is an alkyl-oxy radical for which the alkyl radical is a linear or branched $C_1$-$C_{16}$ and preferentially a $C_1$-$C_8$ hydrocarbon-based radical; when the alkoxy group is optionally substituted, this implies that the alkyl group is optionally substituted as defined herein;

d) an "aryl" group represents a fused or non-fused monocyclic or bicyclic carbon-based group comprising from 5 to 12 carbon atoms, preferably from 6 to 10 carbon atoms, and in which at least one ring is aromatic; preferentially, the aryl radical is a phenyl, biphenyl, naphthyl, more preferably a phenyl group;

e) the term "at least one" is equivalent to the term "one or more"; and f) the term "inclusive" for a range of concentrations means that the limits of that range are included in the defined range.

The salts of the compounds of formula (I), (I'), (Ia) or (Ia') comprises the conventional non-toxic salts of said compounds, such as those formed from organic or inorganic acid or from organic or inorganic base.

As salts of the compounds of formula (I), (I'), (Ia) or (Ia') mention may be made of the salts obtained by addition of the compound of formula (I) to i) a mineral base, such as sodium hydroxide, potassium hydroxide, calcium hydroxide, ammonium hydroxide, magnesium hydroxide, lithium hydroxide, and sodium, potassium or calcium carbonate or hydrogen carbonate for example; or ii) an organic base such as a primary, secondary or tertiary alkylamine, for example triethylamine or butylamine. This primary, secondary or tertiary alkylamine may comprise one or more nitrogen and/or oxygen atoms and may thus comprise, for example, one or more alcohol functions; mention may be made in particular of 2-amino-2-methylpropanol, ethanolamine, triethanolamine, 2-dimethylaminopropanol, 2-amino-2-(hydroxymethyl)-1,3-propanediol and 3-(dimethylamino) propylamine.

Mention may also be made of the salts of amino acids, for instance lysine, arginine, guanidine, glutamic acid and aspartic acid. Advantageously, the salts of the compounds of formula (I) (when it comprises a carboxy group) may be chosen from alkali metal or alkaline-earth metal salts such as sodium, potassium, calcium or magnesium salts and ammonium salts.

As "organic or inorganic acid salt" is more particularly chosen from salts chosen from a salt derived from i) hydrochloric acid HCl, ii) hydrobromic acid HBr, iii) sulfuric acid $H_2SO_4$, iv) alkylsulfonic acids: Alk-$S(O)_2OH$ such as methanesulfonic acid and ethanesulfonic acid; v) arylsulfonic acids: Ar—$S(O)_2OH$ such as benzenesulfonic acid and toluenesulfonic acid; vi) citric acid; vii) succinic acid; viii) tartaric acid; ix) lactic acid; x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3C(O)OH$; xiv) triflic acid $CF_3SO_3H$; and xv) tetrafluoroboric acid $HBF_4$.

The acceptable solvates of the compounds described in the specification comprise conventional solvates such as those formed during the preparation of said compounds owing to the presence of solvents. Mention may be made, by way of example, of the solvates due to the presence of water or of linear or branched alcohols, such as ethanol or isopropanol.

The optical isomers of formula (I) or (I') are in particular, the enantiomers and the diastereoisomers.

The mesomeric forms of formula (II) represents isomers of compounds of formula (II) resulting due to electron delocalization around the hetero atoms such as oxygen and/or sulphur.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods and materials are now described. All publications mentioned herein are incorporated herein by reference.

The present disclosure is not to be limited in scope by the specific embodiments described herein, which are intended for the purposes of exemplification only. Functionally equivalent products, compositions, and methods are clearly within the scope of the disclosure, as described herein.

Composition

The present invention provides a composition, preferably a cosmetic composition including at least one compound corresponding to the following formula (I) or (I'), referred to as "compound of thiopyridinone type" or "thiopyridinone compound". The present invention provides cosmetic compositions which include a combination of compound of thiopyridinone type (I) or (I') with at least one reducing agent of formula (II) and arginine, that shows an increased stability, in particular an improved photostability, of the thiopyridinone compounds and of the cosmetic composition comprising the same. The present invention provides methods for improving the stability of compound(s) of thiopyridinone type (I) or (I') in the cosmetic compositions that are useful for treating a keratin material, for example, the skin of the face and neck of a human. The term "stability" of the thiopyridinone compound can be determined by the change in the amount of the thiopyridinone compound in the composition according to the present invention, during a certain period of time. The term "photostability" of the thiopyridinone compound can be determined by the change in the amount of the thiopyridinone compound in the composition according to the present invention after exposure to light. An increased "stability", or "photostability", means that the change in the amount of the thiopyridinone compound over time is more limited, in particular after exposure of the composition comprising the thiopyridinone compound to light.

Also, the present invention provides non-therapeutic methods of treating the skin comprising application of the cosmetic composition of the present invention on the skin to cause brightening or whitening effect. The cosmetic compositions are additionally useful in non-therapeutic methods for treating dark spots, and uneven skin texture.

Thiopyridinone Compound

According to an embodiment the present invention provides a composition, preferably a cosmetic composition, comprising:

i. at least one compound selected from a compound of Formula (I) below, its tautomer of formula (I') below; salts, solvates, hydrates, optical isomers, racemates, or mixtures thereof:

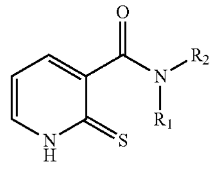

Formula (I)

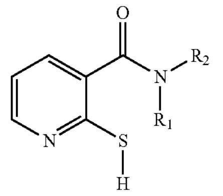

Formula (I')

wherein, $R_1$ denotes a radical chosen from:

a) a hydrogen atom; and b) a saturated linear $C_1$-$C_{10}$ or branched $C_3$-$C_{10}$ alkyl group optionally substituted with one or more groups, which may be identical or different, chosen from:

i) —O—$R_3$;

ii) —S—$R_3$;

$R_2$ denotes a radical chosen from:

a) a hydrogen atom;

b) a saturated linear $C_1$-$C_{12}$ or branched $C_3$-$C_{12}$ or cyclic $C_3$-$C_8$ hydrocarbonated group, optionally substituted with one or more groups, which may be identical or different, chosen from:

i) —O—$R_3$;

ii) —S—$R_3$;

iii) —C(O)—O—$R_3$;

iv) a $C_5$-$C_{12}$ aryl group optionally substituted with one or more hydroxyls and/or with one or more $C_1$-$C_8$ alkoxy radicals, and c) a $C_5$-$C_{12}$ aryl group optionally substituted with one or more hydroxyls and/or with one or more $C_1$-$C_8$alkoxy radicals;

$R_3$ denotes a radical chosen from:

a) a hydrogen atom, and b) a saturated linear $C_1$-$C_{10}$ or branched $C_3$-$C_{10}$ alkyl group;

ii. at least one reducing agent of formula (II) its mesomeric forms, and its solvates such as hydrates (II)

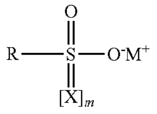

wherein,

X represents a heteroatom selected from oxygen or sulfur, preferably oxygen;

m is 0 or 1;

$M^+$ is a cation, preferably selected from alkali metal, alkaline earth metal or ammonium, more preferably selected from an alkali metal such as sodium or potassium;

R represents a group selected from:

i) —OH, ii) —O-$M'^+$ with $M'^+$ as previously defined for $M^+$, iii)

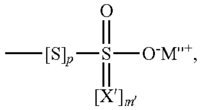

wherein, p is an integer inclusively selected between 0 and 4, preferably 0, 1, 2, and more preferably 0 or 2;

m' is 0 or 1, preferably 1;

X' is as defined for X, preferably X' represents an oxygen atom; and $M''^+$ is as previously defined for $M^+$, and $M^+$, $M'^+$, $M''^+$ are identical or different, preferably identical; and iii. arginine.

The compounds used according to the invention therefore correspond to formula (I) or tautomer (I') below or their salts, their optical isomers, racemates, and/or solvates such as hydrates and the thereof, alone or as a mixture.

(I)

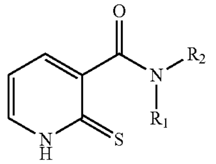

(I')

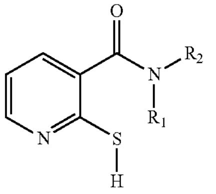

in which Formulas (I) and (I'):

$R_1$ denotes a radical chosen from:

a) a hydrogen atom;

b) a saturated linear $C_1$-$C_{10}$ or branched $C_3$-$C_{10}$ alkyl group optionally substituted with one or more groups, which may be identical or different, chosen from:

i) —O—$R_3$ ii) —S—$R_3$;

$R_2$ denotes a radical chosen from:

a) a hydrogen atom;

b) a saturated linear $C_1$-$C_{12}$ or branched $C_3$-$C_{12}$ or cyclic $C_3$-$C_8$ hydrocarbonated group, optionally substituted with one or more groups, which may be identical or different, chosen from:

i) —O—$R_3$;

ii) —S—$R_3$;

iii) —C(O)—O—$R_3$;

iv) a $C_5$-$C_{12}$ aryl group optionally substituted with one or more hydroxyls and/or with one or more $C_1$-$C_8$ alkoxy radicals; and c) a $C_5$-$C_{12}$ aryl group optionally substituted with one or more hydroxyls and/or with one or more $C_1$-$C_8$ alkoxy radicals wherein $R_3$ denotes a radical chosen from:

a) a hydrogen atom; and b) a saturated linear $C_1$-$C_{10}$ or branched $C_3$-$C_{10}$ alkyl group.

Compound (I') is the tautomer form of compound (I) when a tautomeric equilibrium exists according to the following scheme:

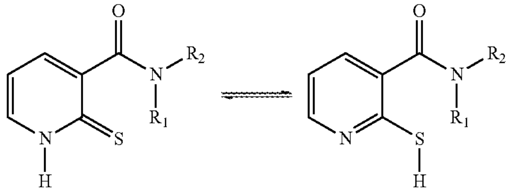

(I) (I')

According to one embodiment of the invention $R_1$ represents one hydrogen atom.

According to another embodiment of the invention $R_1$ represents a linear ($C_1$-$C_{10}$)alkyl group or branched ($C_3$-$C_{10}$)alkyl group, especially a linear ($C_1$-$C_6$)alkyl group or branched ($C_3$-$C_6$)alkyl group, such as methyl, ethyl, n-pentyl, n-nonyl, isobutyl, more preferably ethyl. Particularly the said alkyl group of $R_1$ is not substituted.

According to one embodiment of the invention $R_2$ represents one hydrogen atom.

According to another embodiment of the invention $R_2$ represents a linear ($C_1$-$C_{10}$)alkyl group or branched ($C_3$-$C_{10}$)alkyl group, especially a linear ($C_1$-$C_6$)alkyl group or branched ($C_3$-$C_6$)alkyl group, such as methyl, ethyl, n-pentyl, n-nonyl, isobutyl, more preferably methyl or ethyl group; the said alkyl group of $R_2$ being not substituted.

According to another embodiment of the invention $R_2$ represents a linear ($C_1$-$C_{10}$)alkyl group or branched ($C_3$-$C_{10}$)alkyl group, especially a linear ($C_1$-$C_6$)alkyl group or branched ($C_3$-$C_6$)alkyl group, such as methyl, ethyl, n-pentyl, n-nonyl, isobutyl, more preferably methyl or ethyl; the said alkyl group being substituted by one or more groups selected from i), ii), iii) and iv) as defined above. Preferably the said alkyl group being substituted by one or two groups selected from i), ii) and iii), more preferably by one or two groups selected from i) and iii), better substituted by one group iii) as carboxy.

Another variant for radical $R_2$ is that the said alkyl group being substituted by one group iv) especially substituted by one phenyl group.

According to another embodiment of the invention $R_2$ represents a ($C_3$-$C_8$) cycloalkyl group, preferably a ($C_5$-$C_7$) cycloalkyl group such cyclohexyl.

According to another embodiment of the invention $R_2$ represents $C_5$-$C_{12}$ aryl group optionally substituted with one or more hydroxyls and/or with one or more $C_1$-$C_8$ alkoxy radicals, preferably a phenyl group particularly not substituted.

According to an embodiment $R_3$ represents a hydrogen atom.

According to another embodiment $R_3$ represents a saturated linear $C_1$-$C_{10}$ or branched $C_3$-$C_{10}$ alkyl group; particularly a linear ($C_1$-$C_6$)alkyl group or a branched ($C_3$-$C_6$)alkyl group, preferably ($C_1$-$C_4$)alkyl group such as methyl group.

Preferably, the compounds of formula (I) and tautomer (I') or their salts, their optical isomers, racemates, and/or solvates such as hydrates and the thereof, alone or as a mixture; have the following meanings:

$R_1$ denotes a radical chosen from:
- a) a hydrogen atom;
- b) a saturated linear $C_1$-$C_6$ or branched $C_3$-$C_6$ alkyl group optionally substituted with one or more groups, which may be identical or different, chosen from:
  - i. —O—$R_3$;
  - ii. —S—$R_3$;

preferably optionally substituted with one or more groups i);

$R_2$ denotes a radical chosen from:
- a) a hydrogen atom;
- b) a saturated hydrocarbonated group linear $C_1$-$C_{10}$ or branched $C_3$-$C_{10}$ or cyclic $C_3$-$C_8$ such as C5-C6, optionally substituted with one or more groups, which may be identical or different, chosen from:
  - i. —O—$R_3$;
  - ii. —$SR_3$;
  - iii. —C(O)—O—$R_3$;
  - iv. a phenyl group optionally substituted with one or more hydroxyls and/or with one or more $C_1$-$C_4$ alkoxy radicals such as methoxy;

preferably substituted with one or more groups selected from i) and iii), preferably iii) such as carboxy $R_3$ denotes a radical chosen from:
- a) a hydrogen atom;
- b) a saturated linear $C_1$-$C_6$ or branched $C_3$-$C_6$ alkyl group.

Preferentially, the compounds of formula (I) and tautomer (I') or their salts, their optical isomers, racemates, and/or solvates such as hydrates and the thereof, alone or as a mixture, have the following meanings:

$R_1$ denotes a radical chosen from:
- a) a hydrogen atom;
- b) a saturated linear $C_1$-$C_4$ or branched $C_3$-$C_4$ alkyl group optionally substituted with one or more groups, which may be identical or different, chosen from i) —$OR_3$, more preferably not substituted;

$R_2$ denotes a radical chosen from:
- a) a hydrogen atom;
- b) a linear $C_1$-$C_{10}$ or branched $C_3$-$C_{10}$ or cyclic $C_3$-$C_8$ as $C_5$-$C_6$ saturated hydrocarbonated group, optionally substituted with one or more groups, which may be identical or different, chosen from:
  - i. —O—$R_3$;
  - ii. —C(O)—O—$R_3$;
  - iv. a $C_5$-$C_{12}$ aryl group optionally substituted with one or more hydroxyls and/or with one or more $C_1$-$C_4$ alkoxy radicals;

$R_3$ denotes a radical chosen from:
- a) a hydrogen atom;
- b) a saturated linear $C_1$-$C_4$ or branched $C_3$-$C_4$ alkyl group such as methyl or ethyl.

Preferentially, the compounds of formula (I) and tautomer (I') or their salts, their optical isomers, racemates, and/or solvates such as hydrates and the thereof, alone or as a mixture;

have the following meanings:

$R_1$ is a hydrogen atom; and $R_2$ denotes a radical chosen from:
- a) a hydrogen atom;
- b) a saturated linear $C_1$-$C_5$ or branched $C_3$-$C_5$ or cyclic $C_3$-$C_8$ as C5-C6 hydrocarbonated group, substituted with one or more groups, which may be identical or different, chosen from v) —C(O)—O—$R_3$, preferably substituted with one group iii) —C(O)—O—$R_3$; and $R_2$ is even more preferably a saturated linear $C_1$-$C_4$ or branched $C_3$-$C_4$ hydrocarbonated group substituted with one group iii) —C(O)—$OR_3$, and $R_3$ denotes a radical chosen from:
- a) a hydrogen atom;
- b) a saturated linear $C_1$-$C_4$ or branched $C_3$-$C_4$ alkyl group such as methyl or ethyl.

According to another preferred embodiment, compounds of formula (I) and tautomer (I') are selected among compounds of formula (Ia) and also the tautomers thereof of formula (Ia') below, the salts thereof, the solvates thereof and the optical isomers thereof, and the racemates thereof, alone or as a mixture:

(Ia)

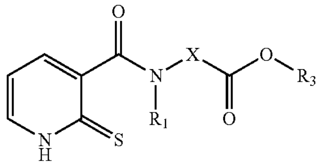

-continued

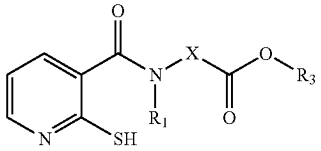

(Ia')

In formula (Ia) and (Ia'), $R_1$ and $R_3$ have the same meaning than for compounds of formula (I) and (I') and X denotes an alkylene radical-$(CH_2)_n$— with n being an integer ranging inclusively from 1 to 10, preferably ranging from 1 to 6, more preferably ranging from 1 to 4, such as 1, preferably $R_3$ represents a hydrogen atom.

Among the compounds of formula (I), the following compounds are preferably used and their tautomer or their salts, their optical isomers, racemates, and/or solvates such as hydrates and the thereof, alone or as a mixture:

| No. | Structure | Chemical name | CAS No. |
|---|---|---|---|
| 1 | 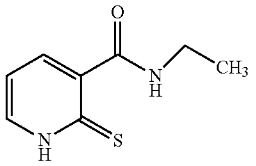 | N-ethyl-2-thioxo-1,2-dihydropyridine-3-carboxamide | 91859-75-5 |
| 2 | 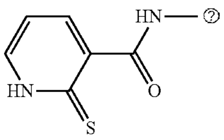 | N-methyl-2-thioxo-1,2-dihydropyridine-3-carboxamide | 91859-74-4 |
| 3 | 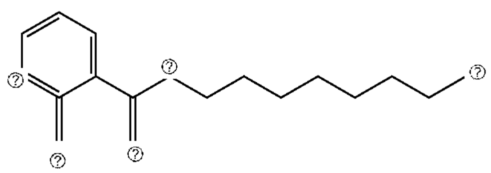 | N-octyl-2-thioxo-1,2-dihydropyridine-3-carboxamide | 91859-77-7 |
| 4 | 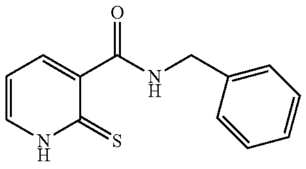 [SMILES: O=C(NCc1ccccc1)c1ccc[nH]c1=S] | N-benzyl-2-thioxo-1,2-dihydropyridine-3-carboxamide | 91859-79-9 |
| 5 | 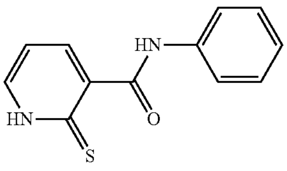 [SMILES: O=C(Nc1ccccc1)c1ccc[nH]c1=S] | N-phenyl-2-thioxo-1,2-dihydropyridine-3-carboxamide | 104857-16-1 |
| 6 | 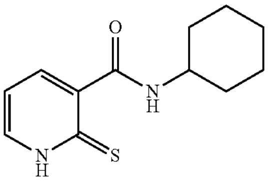 [SMILES: O=C(NC1CCCCC1)c1ccc[nH]c1=S] | N-cyclohexyl-2-thioxo-1,2-dihydropyridine-3-carboxamide | 91859-78-8 |
| 7 | 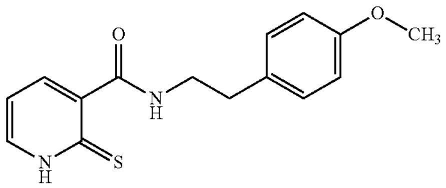 [SMILES: COc1ccc(CCNC(=O)c2ccc[nH]c2=S)cc1] | N-[2-(4-methoxyphenyl)ethyl]-2-thioxo-1,2-dihydropyridine-3-carboxamide | 923682-88-6 |

-continued

| No. | Structure | Chemical name | CAS No. |
|---|---|---|---|
| 8 | 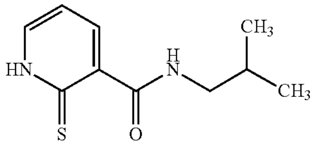 | N-(2-methylpropyl)-2-thioxo-1,2-dihydropyridine-3-carboxamide | 1100027-79-9 |
| 9 | 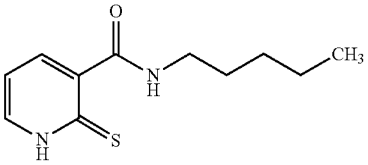 | N-penyl-2-thioxo-1,2-dihydropyridine-3-carboxamide | 330667-57-7 |
| 10 | 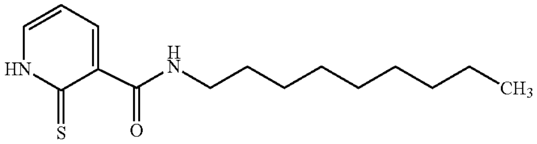 [SMILES: CCCCCCCCCNC(=O)c1ccc[nH]c1=S] | N-nonyl-2-thioxo-1,2-dihydropyridine-3-carboxamide | 1031149-44-6 |
| 11 | 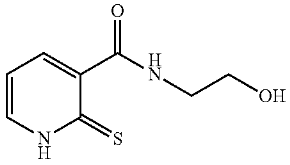 [SMILES: O=C(NCCO)c1ccc[nH]c1=S] | N-(2-hydroxyethyl)-2-thioxo-1,2-dihydropyridine-3-carboxamide | |
| 12 | 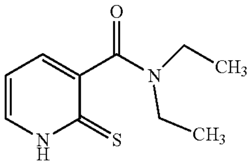 | N,N-diehtyl 2-mercaptonicotinamide | |
| 13 | 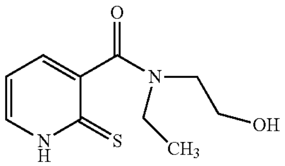 | N-ethyl-N-(2-hydroxyethyl)-2-thioxo-1,2-dihydropyridine-3-carboxamide | |
| 14 | 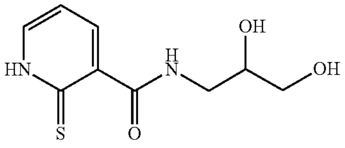 [SMILES: O=C(NCC(O)CO)c1ccc[nH]c1=S] | N-(2,3-dihydroxypropyl)-2-thioxo-1,2-dihydropyridine-3-carboxamide | |
| 15 | 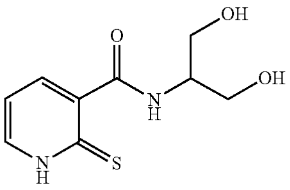 [SMILES: O=C(NC(CO)CO)c1ccc[nH]c1=S] | N-(1,3-dihydroxypropan-2-yl)-2-thioxo-1,2-dihydropyridine-3-carboxamide | |

-continued

| No. | Structure | Chemical name | CAS No. |
|---|---|---|---|
| 16 | 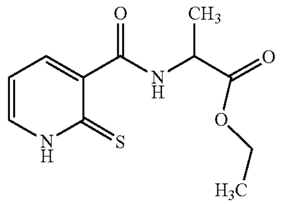 | Ethyl N-[(2-thioxo-1,2-dihydropyridin-3-yl)carbonyl]alaninate | |
| 17 | 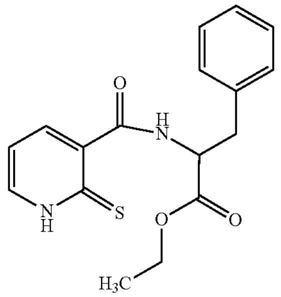 [SMILES: CCOC(=O)C(Cc1ccccc1)NC(=O)c1ccc[nH]c1=S] | Ethyl N-[(2-thioxo-1,2-dihydropyridin-3-yl)carbonyl]phenyl-alaninate | |
| 18 | 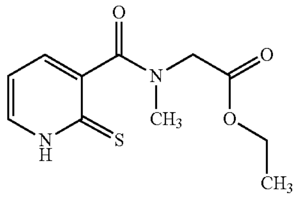 [SMILES: CCOC(=O)CN(C)C(=O)c1ccc[nH]c1=S] | Ethyl N-methyl-N-[(2-thioxo-1,2-dihydropyridin-3-yl)carbonyl]glycinate | |
| 19 | 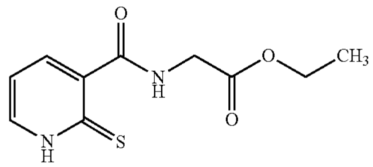 [SMILES: CCOC(=O)CNC(=O)c1ccc[nH]c1=S] | Ethyl N-[(2-thioxo-1,2-dihydropyridin-3-yl)carbonyl]glycinate | |
| 20 | 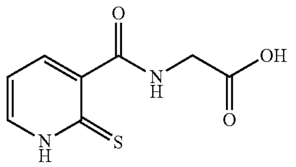 [SMILES: O=C(O)CNC(=O)c1ccc[nH]c1=S] | N-[(2-thioxo-1,2-dihydropyridin-3-yl)carobnyl]glycine | |
| 21 | 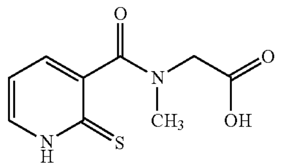 | N-methyl-N-[(2-thioxo-1,2-dihydropyridin-3-yl)carbonyl]glycine | |
| 22 | 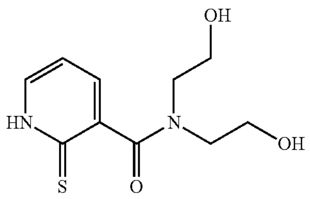 [SMILES: O=C(c1ccc[nH]c1=S)N(CCO)CCO] | N,N-bis(2-hydroxyethyl)-2-thioxo-1,2-dihydropyridine-3-carboxamide | |

-continued

| No. | Structure | Chemical name | CAS No. |
|---|---|---|---|
| 23 | 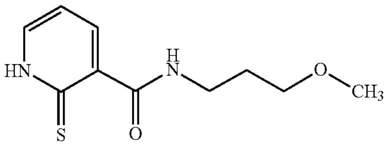 | N-(3-methoxypropyl)-2-thioxo-1,2-dihydropyridine-3-carboxamide | |
| 24 | 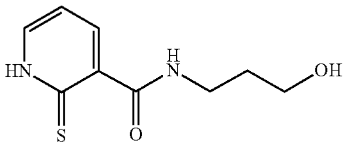 [SMILES: O=C(NCCCO)c1ccc[nH]c1=S] | N-butyl-2-thioxo-1,2-dihydropyridine-3-carboxamide | |

Among these compounds, the following compounds are more particularly preferred:

| No. | Structure | Chemical name | CAS No. |
|---|---|---|---|
| 1 | 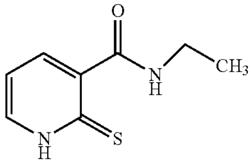 | N-ethyl-2-thioxo-1,2-dihydropyridine-3-carboxamide | 91859-75-5 |
| 2 | 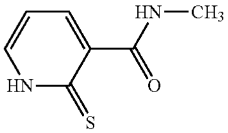 | N-methyl-2-thioxo-1,2-dihydropyridine-3-carboxamide | 1859-74-4 |
| 4 | 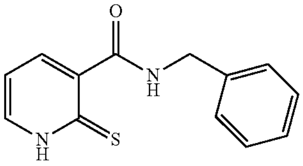 [SMILES: O=C(NCc1ccccc1)c1ccc[nH]c1=S] | N-benzyl-2-thioxo-1,2-dihydropyridine-3-carboxamide | 91859-79-9 |
| 6 | 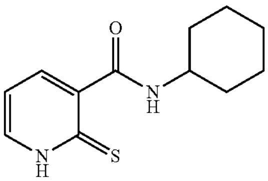 [SMILES: O=C(NC1CCCCC1)c1ccc[nH]c1=S] | N-cyclohexyl-2-thioxo-1,2-dihydropyridine-3-carboxamide | 91859-78-8 |
| 7 | 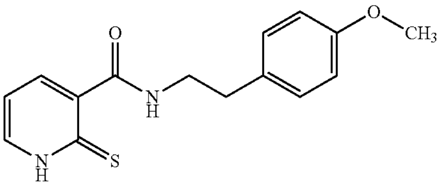 [SMILES: COc1ccc(CCNC(=O)c2ccc[nH]c2=S)cc1] | N-[2-(4-methoxyphenyl)ethyl]-2-thioxo-1,2-dihydropyridine-3-carboxamide | 923682-88-6 |
| 9 | 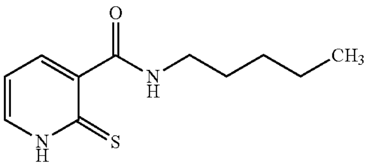 | N-pentyl-2-thioxo-1,2-dihydropyridine-3-carboxamide | 330667-57-7 |

-continued

| No. | Structure | Chemical name | CAS No. |
|---|---|---|---|
| 11 | 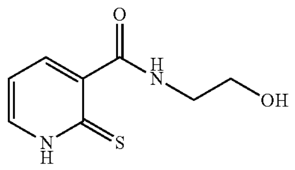 [SMILES: O=C(NCCO)c1ccc[nH]c1=S] | N-(2-hydroxyethyl)-2-thioxo-1,2-dihydropyridine-3-carboxamide | |
| 12 | 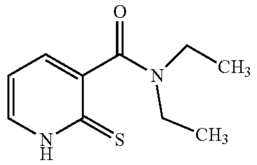 | N,N-diethyl 2-mercaptonicotinamide | |
| 14 | 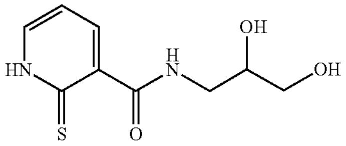 [SMILES: O=C(NCC(O)CO)c1ccc[nH]c1=S] | N-(2,3-dihydroxypropyl)-2-thioxo-1,2-dihydropyridine-3-carboxamide | |
| 15 | 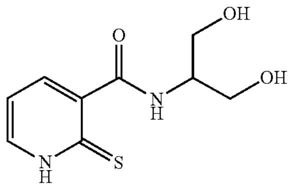 [SMILES: O=C(NC(CO)CO)c1ccc[nH]c1=S] | N-(1,3-dihydroxypropan-2-yl)-2-thioxo-1,2-dihydropyridine-3-carboxamide | |
| 16 | 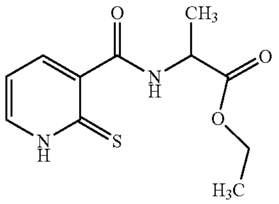 [SMILES: CCOC(=O)C(C)NC(=O)c1ccc[nH]c1=S] | Ethyl N-[(2-thioxo-1,2-dihydropyridin-3-yl)carbonyl]alaninate | |
| 17 | 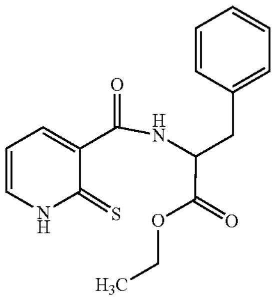 [SMILES: CCOC(=O)C(Cc1ccccc1)NC(=O)c1ccc[nH]c1=S] | Ethyl N-[(2-thioxo-1,2-dihydropyridin-3-yl)carbonyl]phenyl-alaninate | |
| 18 | 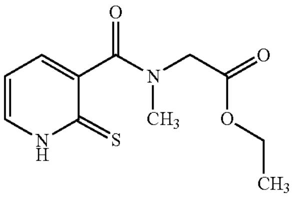 [SMILES: CCOC(=O)CN(C)C(=O)c1ccc[nH]c1=S] | Ethyl N-methyl-N-[(2-thioxo-1,2-dihydropyridin-3-yl)carbonyl]glycinate | |

-continued

| No. | Structure | Chemical name | CAS No. |
|---|---|---|---|
| 19 | 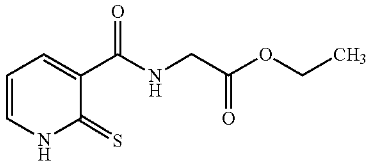 [SMILES: CCOC(=O)CNC(=O)c1ccc[nH]c1=S] | Ethyl N-[(2-thioxo-1,2-dihydropyridin-3-yl)carbonyl]glycinate | |
| 20 | 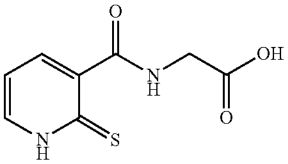 [SMILES: O=C(O)CNC(=O)c1ccc[nH]c1=S] | N-[(2-thioxo-1,2-dihydropyridin-3-yl)carbonyl]glycine | |
| 21 | 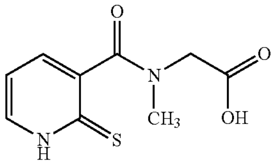 | N-methyl-N-[(2-thioxo-1,2-dihydropyridin-3-yl)carbonyl]glycine | |

More preferably, Among these compounds, the following compounds are more particularly preferred:

| No. | Structure | Chemical name | CAS No. |
|---|---|---|---|
| 1 | 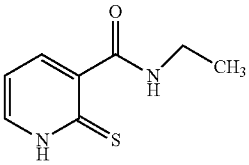 | N-ethyl-2-thioxo-1,2-dihydropyridine-3-carboxamide | 91859-75-5 |
| 9 | 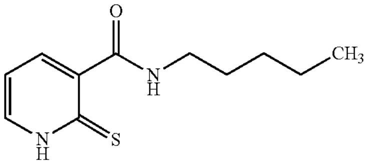 | N-pentyl-2-thioxo-1,2-dihydropyridine-3-carboxamide | 330667-57-7 |
| 16 | 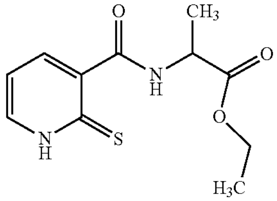 [SMILES: CCOC(=O)C(C)NC(=O)c1ccc[nH]c1=S] | Ethyl N-[(2-thioxo-1,2-dihydropyridin-3-yl)carbonyl]alaninate | |
| 18 | 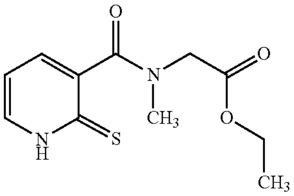 [SMILES: CCOC(=O)CN(C)C(=O)c1ccc[nH]c1=S] | Ethyl N-methyl-N-[(2-thioxo-1,2-dihydropyridin-3-yl)carbonyl]glycinate | |

-continued

| No. | Structure | Chemical name | CAS No. |
|---|---|---|---|
| 19 | 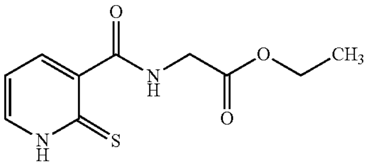 [SMILES: CCOC(=O)CNC(=O)c1ccc[nH]c1=S] | Ethyl N-[(2-thioxo-1,2-dihydropyridin-3-yl)carbonyl]glycinate | |
| 20 | 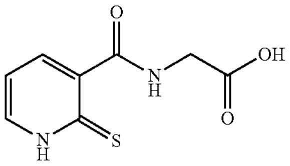 [SMILES: O=C(O)CNC(=O)c1ccc[nH]c1=S] | N-[(2-thioxo-1,2-dihydropyridin-3-yl)carbonyl]glycine | |
| 21 | 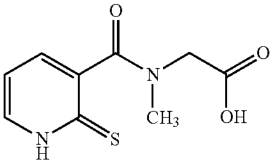 | N-methyl-N-[(2-thioxo-1,2-dihydropyridin-3-yl)carbonyl]glycine | |

Even more preferably, among these compounds, the following compounds are more particularly preferred:

| No. | Structure | Chemical name | CAS No. |
|---|---|---|---|
| 18 | 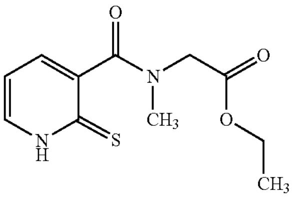 | Ethyl N-methyl-N-[(2-thioxo-1,2-dihydropyridin-3-yl)carbonyl]glycinate | |
| 19 | 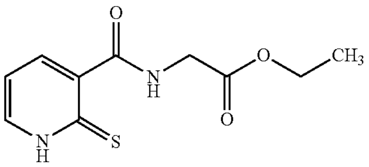 [SMILES: CCOC(=O)CNC(=O)c1ccc[nH]c1=S] | Ethyl N-[(2-thioxo-1,2-dihydropyridin-3-yl)carbonyl]glycinate | |
| 20 | 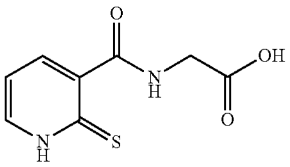 [SMILES: O=C(O)CNC(=O)c1ccc[nH]c1=S] | N-[(2-thioxo-1,2-dihydropyridin-3-yl)carbonyl]glycine | |
| 21 | 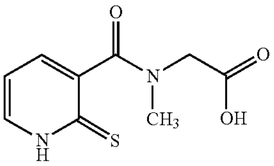 | N-methyl-N-[(2-thioxo-1,2-dihydropyridin-3-yl)carbonyl]glycine | |

In a most preferred embodiment, the compound according to the present invention is the following:

20

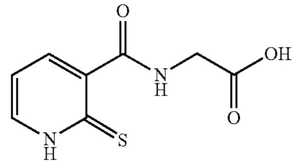 [SMILES: O=C(O)CNC(=O)c1ccc[nH]c1=S]

N-[(2-tioxo-1,2-dihydropyridin-3-yl)carbonyl]glycine

All the compounds above can be obtained by a chemical method known by man skilled in the art, from commercially available reagents.

The (1) thiopyridinone compound of formula (I) or (I') can be prepared in accordance with the process described in, for example, EP-A-3 390 363 or WO 2017/102349.

The (1) thiopyridinone compound may be an active ingredient or active compound in cosmetics or dermatological products. The term "active" ingredient or compound used herein means an ingredient or compound which has a cosmetic or dermatological active property, such as anti-oxidant, whitening, UV-filtering effects and anti-bacterial effects. The (1) thiopyridinone compound used in the present invention can function as a depigmenting, brightening, bleaching or whitening agent, and thus the composition according to the present invention may be used as a skin brightening product or as a cosmetic composition for a brightening keratin material.

The (1) thiopyridinone compound may be used as an agent for depigmenting, brightening, bleaching, or whitening the skin, body hairs, the eyelashes or head hair, and also the lips and/or the nails, and preferably the skin, in particular for eliminating pigmentation spots or senescence spots and/or as an anti-tanning agent.

According to an embodiment of the present invention, the amount of the (1) thiopyridinone compound(s) in the composition may be 0.01% by weight or more, preferably 0.05% by weight or more, and more preferably 0.1% by weight or more, relative to the total weight of the composition.

According to an embodiment of the present invention, the amount of the (1) thiopyridinone compound(s) in the composition may be 10% by weight or less, preferably 5% by weight or less, and more preferably 3% by weight or less, relative to the total weight of the composition.

According to an embodiment of the present invention, the amount of the (1) thiopyridinone compound(s) in the composition according to the present invention may range from 0.01% to 10% by weight, preferably from 0.05% to 5% by weight, and more preferably from 0.1% to 3% by weight, relative to the total weight of the composition.

According to another embodiment of the present invention, the amount of the (1) thiopyridinone compound(s) in the composition may range from 0.01% to 10% by weight, preferably from 0.1% to 5% by weight, and more preferably from 0.5% to 3% by weight, relative to the total weight of the composition.

The composition according to the present invention comprises (1) at least one thiopyridinone compound. Two or more (1) thiopyridinone compounds may be used in combination. Thus, a single type of (1) thiopyridinone compound or a combination of different types of (1) thiopyridinone compounds may be used.

The (1) thiopyridinone compound is selected from compounds of formula (I) below, tautomers of formula (I') below, salts thereof, solvates, such as hydrates, thereof, optical isomers thereof, racemates thereof, and mixtures thereof:

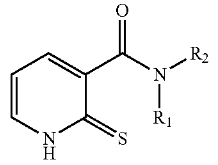

(I)

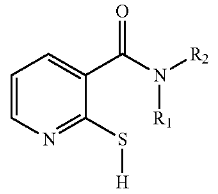

(I')

wherein in formulas (I) and (I'):

$R_1$ denotes a radical chosen from:
- a) a hydrogen atom;
- b) a saturated linear $C_1$-$C_{10}$ or branched $C_3$-$C_{10}$ alkyl group optionally substituted with one or more groups, which may be identical or different, chosen from:
  - i) —O—$R_3$;
  - ii) —S—$R_3$;

$R_2$ denotes a radical chosen from:
- a) a hydrogen atom;
- b) a saturated linear $C_1$-$C_{12}$ or branched $C_3$-$C_{12}$ or cyclic $C_3$-$C_8$ hydrocarbonated group, optionally substituted with one or more groups, which may be identical or different, chosen from:
  - i. —O—$R_3$;
  - ii. —S—$R_3$;
  - iii. —C(O)—O—$R_3$;
  - iv. a $C_5$-$C_{12}$ aryl group optionally substituted with one or more hydroxyls and/or with one or more $C_1$-$C_8$ alkoxy radicals; and
- c) a $C_5$-$C_{12}$ aryl group optionally substituted with one or more hydroxyls and/or with one or more $C_1$-$C_8$ alkoxy radicals wherein $R_3$ denotes a radical chosen from:
- a) a hydrogen atom; and
- b) b) a saturated linear $C_1$-$C_{10}$ or branched $C_3$-$C_{10}$ alkyl group.

Reducing Agent

According to an embodiment of the present invention, the composition comprises at least one (2) reducing agent of formula (II), its mesomeric forms, and its solvates such as hydrates

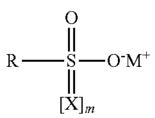

(II)

wherein,

X represents a heteroatom selected from oxygen or sulfur, preferably oxygen;

m is 0 or 1;

$M^+$ is a cation, preferably selected from alkali metal, alkaline earth metal or ammonium, more preferably selected from an alkali metal such as sodium or potassium;

R represents a group selected from:

i) —OH, ii) —O-$M'^+$ with $M'^+$ as previously defined for $M^+$;

iii)

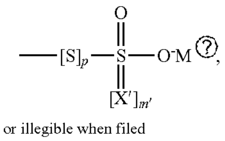

ⓘ indicates text missing or illegible when filed wherein, p is an integer inclusively selected between 0 and 4, preferably 0, 1, 2, and more preferably 0 or 2;

m' is 0 or 1, preferably 1;

X' is as defined for X, preferably X' represents an oxygen atom; and $M''^+$ is as previously defined for $M^+$, and $M^+$, $M'^+$, $M''^+$ are identical or different, preferably identical.

According to another embodiment of the present invention, the composition comprises at least one (2) reducing agent of formula (II) wherein X of formula (II) represents a heteroatom selected from oxygen or sulfur, preferably oxygen;

m of formula (II) is 0 or 1;

$M^+$ of formula (II) is a cation, preferably is sodium or potassium;

R of formula (II) represents a group selected from i) —OH, ii) —O-$M'^+$ with $M'^+$ as previously defined for $M^+$, iii)

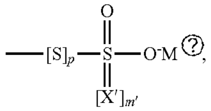

ⓘ indicates text missing or illegible when filed wherein, p is 0 or 2;

m is 0 or 1;

X' is as defined for X, preferably X' represents an oxygen atom; and $M^+$, $M'^+$, $M''^+$ are identical.

According to an embodiment of the present invention, wherein in the (2) reducing agent of formula (II)

R represents a group selected from i) —OH, ii) —O-$M'^+$ with $M'^+$,

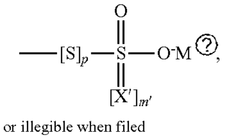

ⓘ indicates text missing or illegible when filed wherein, p is 0 or 2;

m' is 0 or 1;

X' is represents an oxygen atom; and $M^+$, $M'^+$, and $M''^+$ are identical selected from sodium or potassium.

According to an embodiment of the present invention, wherein in the (2) reducing agent of formula (II)

X of formula (II) represents sulphur;

m of formula (II) is 1;

$M^+$ of formula (II) is sodium or potassium;

R of formula (II) represents a group selected from i. —OH, and ii. —O$M'^+$ with $M'^+$, $M^+$, and $M'^+$ are identical.

According to an embodiment, the compounds of formula (II) can be found in their borderline or delocalized mesomeric limit forms, when m=0 thus $R—S(O^-M^+)=O\leftarrow\ \rightarrow R—S(=O)—O^-M^+$ and when m=1 thus the mesomeric limit forms are $$R—S(O^-M^+)(=X)_m=O\leftarrow\ \rightarrow R—S(=O)(=X)_m—O^-M^+\leftarrow\ \rightarrow R—S(=O)(X^-M^+)_m=O$$

wherein, M+, M'+, M"+ are present to ensure the electroneutrality of the molecule of formula (II).

According to a preferred embodiment of the present invention, the (2) reducing agent may be selected from sodium bisulfite, sodium metabisulfite, sodium sulfite, sodium thiosulfate, sodium sulfate, potassium metabisulfite, potassium sulfite, potassium thiosulfate, potassium sulfate, or potassium tetra thionate.

According to another preferred embodiment of the present invention, the (2) reducing agent may be selected from sodium bisulfite, sodium metabisulfite, sodium sulfite, sodium thiosulfate, or sodium sulfate.

According to an embodiment of the present invention, the amount of the (2) reducing agent in the composition may be 0.01% by weight or more, preferably 0.02% by weight or more, and more preferably 0.03% by weight or more, relative to the total weight of the composition.

According to an embodiment of the present invention, the amount of the (2) reducing agent in the composition may be 2.0% by weight or less, preferably 1.0% by weight or less, and more preferably 0.05% by weight or less, relative to the total weight of the composition.

According to an embodiment of the present invention, the amount of the (2) reducing agent in the composition according to the present invention may be from 0.01% to 2% by weight, preferably from 0.02% to 1.0% by weight, and more preferably from 0.03% to 0.5% by weight, relative to the total weight of the composition.

Arginine

According to an embodiment of the present invention, the composition comprises (3) arginine.

According to an embodiment of the present invention, the amount of the ((3) arginine in the composition may be 0.01% by weight or more, preferably 0.1% by weight or more, and more preferably 0.2% by weight or more, relative to the total weight of the composition.

According to an embodiment of the present invention, the amount of the (3) arginine in the composition may be 10.0% by weight or less, preferably 8.0% by weight or less, and more preferably 6.0% by weight or less, relative to the total weight of the composition.

According to an embodiment of the present invention, the amount of the (3) arginine in the composition according to the present invention may be from 0.01% to 10% by weight, preferably from 0.1% to 8% by weight, and more preferably from 0.2% to 6% by weight, relative to the total weight of the composition.

pH Adjusting Agent

According to an embodiment of the present invention, the composition may comprise at least one pH Adjusting Agent (pH adjuster). Two or more pH adjusting agents may be used in combination. Thus, a single type of pH adjusting agent or a combination of different types of pH adjusting agents may be used.

As the pH adjusting agent, at least one acidifying agent and/or at least one basifying agent (alkaline agent) may be used.

The acidifying agent may be a monovalent or polyvalent, such as divalent acid.

The acidifying agents can be, for example, mineral (inorganic) acids such as hydrochloric acid, sulfuric acid, phosphoric acid, or organic acids such as carboxylic acids, for instance tartaric acid, citric acid, and lactic acid, as well as sulphonic acids.

The basifying agent may be a monovalent or polyvalent, such as divalent, base. The basifying agents may be mineral (inorganic) or organic, or hybrid.

The mineral basifying agents may be chosen from aqueous ammonia; alkali metal carbonates or bicarbonates such as sodium or potassium carbonates and sodium or potassium bicarbonates; alkali metal hydroxides such as sodium hydroxide and potassium hydroxide; and mixtures thereof.

The organic basifying agents may be chosen from organic amines with a pkb at 25° C. of less than 12, preferably less than 10, and even more advantageously less than 6. It should be noted that it is the pKb corresponding to the function of highest basicity. In addition, the organic amines do not comprise any alkyl or alkenyl fatty chains comprising more than ten carbon atoms.

The organic basifying agent may be chosen, for example, from alkanolamines, oxyethylenated and/or oxypropylenated ethylenediamines, amino acids and amine compounds of formula (III) below:

(III)

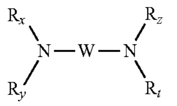

in which

W represents a $C_1$-$C_6$ divalent alkylene radical optionally substituted with one or more hydroxyl groups or a $C_1$-$C_6$ alkyl radical, and optionally interrupted with one or more heteroatoms such as O and N, and $R_x$, $R_y$, $R_z$, and $R_t$, which may be identical or different, represent a hydrogen atom or a $C_1$-$C_6$ alkyl, $C_1$-$C_6$ hydroxyalkyl, or $C_1$-$C_6$ aminoalkyl radical.

Examples of the amine compounds of formula (III) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Alkanolamines such as monoalkanolamines, dialkanolamines or trialkanolamines comprising one to three identical or different $C_1$-$C_4$ hydroxyalkyl radicals may be suitable for the present invention. Among the compounds of this type, mention may be made of monoethanolamine (MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino) methane.

Amino acids that may be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

It may be preferable that the amino acids are basic amino acids comprising an additional amine function optionally included in a ring or in an ureido function.

Such basic amino acids may preferably be chosen from those corresponding to formula (IV) below:

(IV)

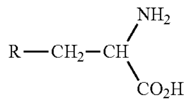

in which

R of formula (IV) represents a group chosen from:

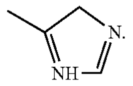

$-(CH_2)_3-NH_2$, $-(CH_2)_2-NH_2$, $-(CH_2)_2-NH-CO-NH_2$, and

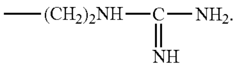

The compounds corresponding to formula (IV) include histidine, lysine, arginine, ornithine and citrulline.

The organic basifying agent may be chosen from organic amines of heterocyclic type. Besides histidine that has already been mentioned in the amino acids, mention may in particular be made of pyridine, piperidine, imidazole, triazole, tetrazole and benzimidazole.

The organic basifying agent may also be chosen from amino acid dipeptides. As amino acid dipeptides that may be used in the present invention, mention may be made especially of carnosine, anserine and baleine.

The organic basifying agent may also be chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethyl-guanidine, glycocyamine, metformin, agmatine, N-amidinoalanine, 3-guanidino-propionic acid, 4-guanidinobutyric acid and 2-([amino (imino)methyl]amino)ethane-1-sulfonic acid.

In a preferred embodiment of the present invention, the organic basifying agent may be selected from amino acids, preferably basic amino acids, and more preferably arginine, lysine, histidine or mixtures thereof. Even more preferentially, the organic basifying agent may be arginine.

Hybrid compounds that may be mentioned include the salts of the amines mentioned previously with acids such as carbonic acid or hydrochloric acid. Guanidine carbonate or monoethanolamine hydrochloride may be used in particular.

According to an embodiment of the present invention, the amount of the pH adjusting agent in the composition may be equal to or more than 0.01% by weight, preferably 0.05% by weight or more, and more preferably 0.1% by weight or more, relative to the total weight of the composition.

According to an embodiment of the present invention, the amount of the pH adjusting agent in the composition may be in an amount equal to or less than 15% by weight or less, preferably 10% by weight or less, and more preferably 5% by weight or less, relative to the total weight of the composition.

According to an embodiment of the present invention, the pH adjusting agent may be present in an amount ranging from 0.01% to 15% by weight, preferably from 0.05% to 10% by weight, and more preferably from 0.1% to 5% by weight or less, relative to the total weight of the composition.

It is preferable that the composition according to the present invention have a pH of 4.5 or more, and more preferably 5 or more.

It is preferable that the composition according to the present invention have a pH of 6.5 or less, and more preferably 6 or less.

It is preferable that the composition according to the present invention have a pH of from 4.5 to 6.5, and more preferably from 5 to 6.

The pH of the composition means the pH of the aqueous phase of the composition according to the present invention.

It may be preferable that at least one buffer or buffering agent also be used, as the pH adjusting agent, in combination with the acidifying agent and/or the basifying agent, in order to stabilize the pH of the composition according to the present invention.

As the buffer, any of commonly known buffers may be used. For example, salts of acids or bases, preferably salts of weak acids or weak bases, may be used. For example, sodium citrate or sodium lactate may be used as the buffer, if citric acid or lactic acid is used as the acidifying agent.

Water

According to an embodiment of the present invention, the composition may advantageously comprise at least one medium/solvent, including water and/or organic medium/solvent.

According to an embodiment of the present invention, the composition may comprise water in varying amounts. For low viscosity applications of the composition, e.g., in form of leave-on lotion, a relatively high amount of water may be used. For example, water is used in a content of greater than or equal to 20% by weight relative to the total weight of composition. The water content in the low viscosity composition according to the invention preferably ranges from 20% to 99% by weight, or preferably from 30% to 95% by weight, or from 40% to 90% by weight, relative to the total weight of the composition. For high viscosity applications of the composition, e.g., in form of leave-on cream, a relatively lower amount of water may be used. The high viscosity composition according to the invention advantageously comprises water in a content of less than or equal to 40% by weight relative to the total weight of composition.

According to an embodiment of the present invention, the amount of water in the composition may be present in an amount of 20% by weight or more, preferably 30% by weight or more, and more preferably 40% by weight or more, relative to the total weight of the composition.

According to an embodiment of the present invention, the amount of water in the composition may be present in an amount of 99% by weight or less, preferably 95% by weight or less, and more preferably 90% by weight or less, relative to the total weight of the composition.

According to an embodiment of the present invention, the amount water in the composition according to the present invention may be from 20% to 99% by weight, preferably from 30% to 95% by weight, and more preferably from 40% to 90% by weight, relative to the total weight of the composition.

The composition according to the invention may also comprise one or more organic medium/solvents, preferably water-soluble organic medium/solvents (solubility of greater than or equal to 5% in water at 25° C. and at atmospheric pressure).

Examples of the organic medium/solvents that may be mentioned include alcohols: in particular monovalent alcohols such as ethyl alcohol, isopropyl alcohol, benzyl alcohol, and phenylethyl alcohol; diols such as ethylene glycol, propylene glycol, and butylene glycol; other polyols such as glycerol, sugar and sugar alcohols; and ethers such as ethylene glycol monomethyl, monoethyl, and monobutyl ethers, propylene glycol monomethyl, monoethyl, and monobutyl ether, and butylene glycol monomethyl, monoethyl, and monobutyl ethers.

The organic medium/solvents, when they are present in an amount ranging from 0.1% to 40% by weight, preferably from 1% to 30% by weight, or from 5% to 20% by weight, relative to the total weight of the composition according to the invention.

According to an embodiment of the present invention, the composition brightens or depigments a keratin material, preferably skin.

According to an embodiment of the present invention, the composition may be useful for whitening or depigmenting a keratin material, preferably skin.

Preparation of the Composition

According to an embodiment of the present invention there is provided a process for preparing the composition. The process comprises mixing the above described essential and optional components by any known method. In an embodiment the composition of the present invention may be prepared by a process including the steps of: mixing at least one compound of formula (I) or (I'), at least one reducing agent, arginine with water. Mixing include addition of other additives as required. The process involves mixing the components at any temperature, preferably at room temperature, more preferably at 30° C. or more, at 40° C. or more and more preferably at 50° C. or more.

The compositions according to the invention can be manufactured by known processes, generally used in the cosmetic or dermatological field.

The composition of the according to the present invention may be in various forms but not limited to emulsion, solution, gel, or cream.

Method/Use of the Composition

According to an embodiment the present invention provides a cosmetic method of treating a keratin material, the method comprising: applying the composition of the present invention on the keratin material, preferably skin.

According to an embodiment the present invention provides a non-therapeutic method of treating a keratin material, the method comprising: applying the composition of the present invention on the keratin material, preferably skin.

According to an embodiment the present invention provides use of the composition brightening or depigmenting a keratin material, preferably skin. In another embodiment, the composition is suitable for the treatment of darker and/or more coloured spots on the skin. In one another embodiment, the composition is useful in providing necessary care to the skin, preferably brightening the skin, and/or reducing or lightening darker and/or more coloured spots on the skin.

The composition according to the present invention is a cosmetic composition may be applied once per day, twice per day, or more than once or twice per day. In some cases, the composition is applied in the evenings before bed. In other cases, the compositions are applied in the morning. In still other cases, the composition may be applied immediately after washing the skin. The compositions may be used once, or for a series of days, weeks, or months. For example, the compositions may be used daily for a period of 1, 2, 3, 4, 5, 6, 7, 8 or more weeks, or months.

According to an embodiment the present invention provides use of combination of:

(i) at least one reducing agent of formula (II) its mesomeric forms, and its solvates such as hydrates (II)

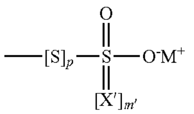

wherein,

X represents a heteroatom selected from oxygen or sulfur, preferably oxygen;

m is 0 or 1;

$M^+$ is a cation, preferably selected from alkali metal, alkaline earth metal or ammonium, more preferably selected from an alkali metal such as sodium or potassium;

R represents a group selected from:

i) —OH, ii) —O-$M'^+$ with $M'^+$ as previously defined for $M^+$, iii)

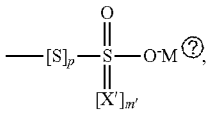

(?) indicates text missing or illegible when filed wherein, p is an integer inclusively selected between 0 and 4, preferably 0, 1, 2, and more preferably 0 or 2;

m' is 0 or 1, preferably 1;

X' is as defined for X, preferably X' represents an oxygen atom; and $M''^+$ is as previously defined for $M^+$, and $M^+$, $M'^+$, $M''^+$ are identical or different, preferably identical, and (ii) arginine, in a composition comprising at least one compound selected from compounds of formula (I), its tautomer of formula (I'), salts, optical isomers, racemates, solvates, hydrates, or mixtures thereof:

(I)

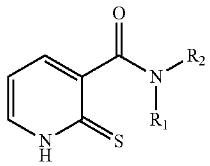

(I')

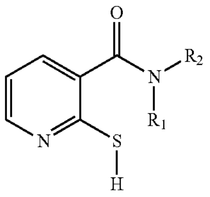

wherein in formulae (I) and (I'):

$R_1$ denotes a radical chosen from:

a) a hydrogen atom;

b) a saturated linear $C_1$-$C_{10}$ or branched $C_3$-$C_{10}$ alkyl group optionally substituted with one or more groups, which may be identical or different, chosen from:

i) —O—$R_3$;

ii) —S—$R_3$;

$R_2$ denotes a radical chosen from:

a) a hydrogen atom;

b) a saturated hydrocarbonated group linear $C_1$-$C_{12}$ or branched $C_3$-$C_{12}$ or cyclic $C_3$-$C_8$, optionally substituted with one or more groups, which may be identical or different, chosen from:

i) —O—$R_3$;

ii) —S—$R_3$;

iii) —C(O)—O—$R_3$;

iv) a $C_5$-$C_{12}$ aryl group optionally substituted with one or more hydroxyls and/or with one or more $C_1$-$C_8$ alkoxy radicals;

c) a $C_5$-$C_{12}$ aryl group optionally substituted with one or more hydroxyls and/or with one or more $C_1$-$C_8$ alkoxy radicals; and $R_3$ denotes a radical chosen from:

a) a hydrogen atom;

b) a saturated linear $C_1$-$C_{10}$ or branched $C_3$-$C_{10}$ alkyl group, to stabilize the compound of formula (I), its tautomer of formula (I'), salts, solvates, hydrates, optical isomers, racemates, or mixtures thereof, in the composition.

The term "stabilize" has the same meaning as enhancing the stability.

According to an embodiment of the present invention, the combination of at least one reducing agent and arginine stabilizes the compound of formula (I) or (I') in the composition. In a particular embodiment, the composition according to the present invention shows increased stability of the thiopyridinone compound of formula (l) and (I') therein. In one embodiment, the composition according to the present invention show increased stability of the compound of formula (I) or (I'), when stored for a longer period of time at room temperature. In another embodiment, the composition according to the present invention shows increased stability, and preferably increased photostability, of the compound of formula (I) or (I'), when the composition is exposed to light. In yet another embodiment, the increased stability, and preferably the increased photostability, of the compound of formula (I) or (I') in the composition provide improved bioavailability to cause prolonged brightening or depigmenting effects on the keratin material.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices, and materials are described herein. It is to be understood that this disclosure is not limited to particular composition, methods, and experimental conditions described, as such methods and conditions may apply. The present invention will be described in a more detailed manner by way of examples. However, these examples should not be construed as limiting the scope of the present invention.

Example 1: Synthesis of Compound 20

Compound 20 is synthesized as disclosed in example 2 of patent EP3 390 363.

Example 2

Compositions for Whitening and Depigmentation of Skin

Composition A (according to the invention) was prepared using the components as described in Table 1 below. 0.50 wt % of Compound 20 of Formula (I) i.e., 2-mercaptonicotinoyl glycine, 0.20 wt % of sodium thiosulphate, 0.50 wt % of Arginine, 0.60 wt % of thickeners, 1.00 wt % of preservatives and other components as mentioned in Table 1, along with water in necessary amount was mixed together to obtain the Composition A. Similarly, Composition B (according to the invention) comprising 3.00 wt % of Arginine and with other components as mentioned in Table 1 was also prepared.

TABLE 1

| Composition INCI (wt %) | A | B |
|---|---|---|
| 2-Mercaptonicotinoyl Glycine | 0.50 | 0.50 |
| Sodium Thiosulfate | 0.20 | 0.20 |
| Arginine | 0.50 | 3.00 |
| Thickeners | 0.60 | 0.60 |
| Preservatives | 1.00 | 1.00 |
| Alcohol Denatured | 4.00 | 4.00 |
| Water | 69.83 | 66.90 |
| Glycols | 6.00 | 6.00 |
| Laureth-4 | 0.50 | 0.50 |
| Polyglyceryl-4 Caprate | 1.00 | 1.00 |

TABLE 1-continued

| Composition INCI (wt %) | A | B |
|---|---|---|
| Silicone oils | 4.20 | 4.20 |
| Actives | 10.30 | 10.30 |
| Caffeine | 1.00 | 1.00 |
| Chelating agent | 0.30 | 0.30 |
| Citric Acid | 0.07 | 0.50 |

Example 3

Photostability of Compositions

The compositions as prepared in Example 1 were analyzed to determine its photostability when exposed to UV radiation.

Each of the inventive compositions A and B was independently coated on an inert support. The coated supports were exposed to UV radiation of 5 J/cm$^2$ for about 1 hour. The exposed compositions were then dissolved in a solvent (organic solvent) and the solutions were analyzed HPLC or UPLC chromatographic methods.

The amount of compound 20 of formula (I) in each of the compositions was measured by HPLC-UV assay at two timings as mentioned below.

Timing (1): Just after the preparation of the composition.

Timing (2): Solution of the compositions after UV exposure.

The details of the HPLC-UV assays are as follows:

| Apparatus/Reagents | |
|---|---|
| HPLC System | Ultra performance LC (UPLC) |
| HPLC Column | RP18, 1.7, 2.1 mm × 100 mm |
| Eluent A | 0.1% phosphoric acid |
| Eluent B | Methanol |

| HPLC Conditions | |
|---|---|
| UV detector | 296 nm |
| Column temp | 30° C. |
| Flow rate | 0.4 mL/min |
| Injection volume | 1 μL |
| Mobile phase | Gradient mode<br>A: 0.1% phosphoric acid in water<br>B: methanol |

The amount of compound 20 of formula (I) remaining in each of the compositions before (Timing 1) and after UV exposure (Timing 2) were determined by HPLC-UV assay and the difference in the amount of compound of formula (I) was computed.

The % values of compound 20 of formula (I), remained in UV exposed compositions A and B are shown in Table 2 below.

TABLE 2

| Composition | Compound 20 of formula (I) remained after UV exposure (wt %) |
|---|---|
| A (inventive) | 80% |
| B (inventive) | 86% |

It was found that the compositions A and B, which comprised arginine were more effective and stable even under exposure to UV radiation. With compositions A and B having 0.5 wt % and 3 wt % arginine respectively, the stabilization of compound 20 was increased in the composition. Thus, the composition according to the present invention comprising arginine, provided a stable composition with increased shelf life.

The invention claimed is:

1. A stable composition comprising:

i) at least one compound chosen from compounds of formula (I), its tautomer of formula (I'), salts thereof, solvates thereof, hydrates thereof, optical isomers thereof, racemates thereof, or mixtures of two or more thereof:

Formula (I)

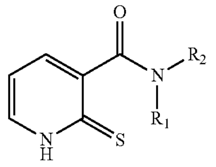

Formula (I')

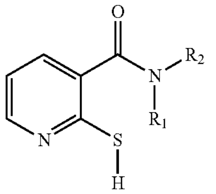

wherein, in formula (I) and formula (I'):

$R_1$ represents a radical chosen from:

a) a hydrogen atom; or b) a saturated linear $C_1$-$C_{10}$ or branched $C_3$-$C_{10}$ alkyl group optionally substituted with one or more groups, which may be identical or different, chosen from:

i) —O—$R_3$; or ii) —S—$R_3$;

$R_2$ represents a radical chosen from:

a) a hydrogen atom; or b) a saturated linear $C_1$-$C_{12}$ or branched $C_3$-$C_{12}$ or cyclic $C_3$-$C_8$ hydrocarbonated group, optionally substituted with one or more groups, which may be identical or different, chosen from:

i) —O—$R_3$;

ii) —S—$R_3$;

iii) —C(O)—O—$R_3$; or iv) a $C_5$-$C_{12}$ aryl group optionally substituted with one or more hydroxyls and/or with one or more $C_1$-$C_8$ alkoxy radicals, or c) a $C_5$-$C_{12}$ aryl group optionally substituted with one or more hydroxyls and/or with one or more $C_1$-$C_8$ alkoxy radicals; and $R_3$ represents a radical chosen from:

a) a hydrogen atom, or b) a saturated linear $C_1$-$C_{10}$ or branched $C_3$-$C_{10}$ alkyl group;

ii) at least one reducing agent of formula (II), its mesomeric forms, its solvates, or hydrates thereof:

(II)

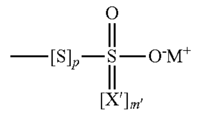

wherein, in formula (II):

X represents a heteroatom chosen from oxygen or sulfur;

m is 0 or 1;

$M^+$ is a cation; and

R represents a group chosen from:

i) —OH, ii) —O-$M'^+$ with $M'^+$ as previously defined for $M^+$, or iii)

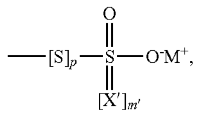

wherein:

p is 0, 1, 2, 3, or 4;

m' is 0 or 1;

X' is as defined for X; and $M''^+$ is as previously defined for $M^+$, wherein $M^+$, $M'^+$, $M''^+$ are identical or different; and iii) arginine, present in an amount ranging from 0.1% to 6% by weight, relative to the total weight of the composition, wherein the total combined amount of ii) and iii) stabilizes the composition.

2. The stable composition according to claim 1, wherein, in formula (I) and formula (I'):

$R_1$ represents a hydrogen atom; or $R_1$ represents a linear ($C_1$-$C_{10}$) alkyl group or branched ($C_3$-$C_{10}$) alkyl group.

3. The stable composition according to claim 1, wherein, in formula (I) and formula (I'):

$R_2$ represents a hydrogen atom; or $R_2$ represents a linear ($C_1$-$C_{10}$) alkyl group or branched ($C_3$-$C_{10}$) alkyl group.

4. The stable composition according to claim 1, wherein, in formula (I) and formula (I'), $R_2$ represents a linear ($C_1$-$C_{10}$) alkyl group or branched ($C_3$-$C_{10}$) alkyl group.

5. The stable composition according to claim 1, wherein, in formula (I) and formula (I'):

$R_2$ represents a ($C_3$-$C_8$) cycloalkyl group; or $R_2$ represents a $C_5$-$C_{12}$ aryl group optionally substituted with one or more hydroxyls and/or with one or more $C_1$-$C_8$ alkoxy radicals.

6. The stable composition according to claim 1, wherein, in formula (I) and formula (I'):

$R_3$ represents a hydrogen atom; or $R_3$ represents a saturated linear $C_1$-$C_{10}$ or branched $C_3$-$C_{10}$ alkyl group.

7. The stable composition according to claim 1, wherein, in formula (I) and formula (I'):

$R_1$ represents a radical chosen from:

a) a hydrogen atom; or b) a saturated linear $C_1$-$C_6$ or branched $C_3$-$C_6$ alkyl group optionally substituted with one or more groups, which may be identical or different, chosen from:

i) —O—$R_3$; or ii) —S—$R_3$;

$R_2$ represents a radical chosen from:

a) a hydrogen atom; or b) a saturated linear $C_1$-$C_{10}$ or branched $C_3$-$C_{10}$ or cyclic $C_3$-$C_8$, optionally substituted with one or more groups, which may be identical or different, chosen from:

i) —O—$R_3$;

ii) —$SR_3$;

iii) —C(O)—O—$R_3$; or iv) a phenyl group optionally substituted with one or more hydroxyls and/or with one or more $C_1$-$C_4$ alkoxy; and $R_3$ represents a radical chosen from:

a) a hydrogen atom; or b) a saturated linear $C_1$-$C_6$ or branched $C_3$-$C_6$ alkyl group.

8. The stable composition according to claim 1, wherein the i) at least one compound is chosen from:

| | |
|---|---|
| 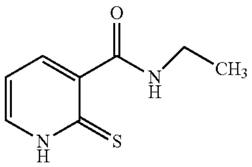 | N-ethyl-2-thioxo-1,2-dihydropyridine-3-carboxamide; |
| 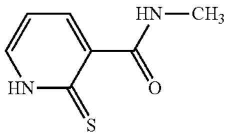 | N-methyl-2-thioxo-1,2-dihydropyridine-3-carboxamide; |
| 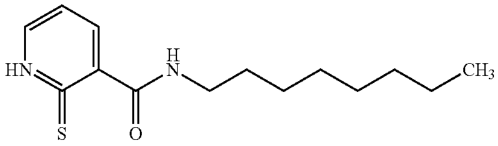 | N-octyl-2-thioxo-1,2-dihydropyridine-3-carboxamide; |
| 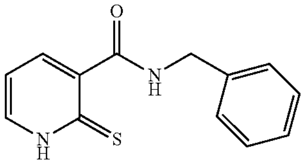 [SMILES: O=C(NCc1ccccc1)c1ccc[nH]c1=S] | N-benzyl-2-thioxo-1,2-dihydropyridine-3-carboxamide; |
| 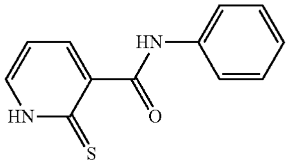 [SMILES: O=C(Nc1ccccc1)c1ccc[nH]c1=S] | N-phenyl-2-thioxo-1,2-dihydropyridine-3-carboxamide; |
| 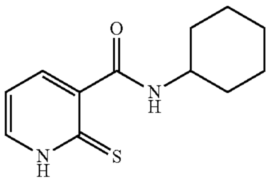 [SMILES: O=C(NC1CCCCC1)c1ccc[nH]c1=S] | N-cyclohexyl-2-thioxo-1,2-dihydropyridine-3 carboxamide; |
| 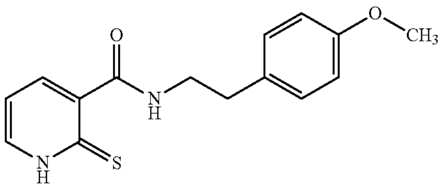 [SMILES: COc1ccc(CCNC(=O)c2ccc[nH]c2=S)cc1] | N-[2-(4-methoxyphenyl)ethyl]-2-thioxo-1,2-dihydropyridine-3-carboxamide; |

-continued

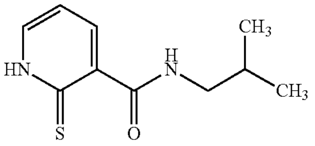

N-(2-methylpropyl)-2-thioxo-1,2-dihydropyridine-3-carboxamide;

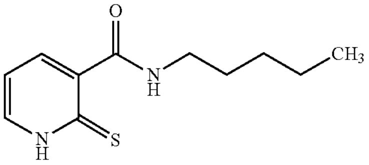

N-pentyl-2-thioxo-1,2-dihydropyridine-3-carboxamide;

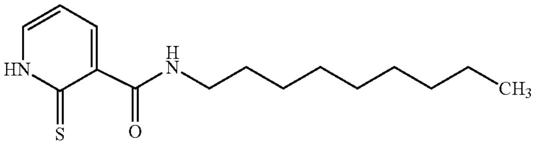 [SMILES: CCCCCCCCCNC(=O)c1ccc[nH]c1=S]

N-nonyl-2-thioxo-1,2-dihydropyridine-3-carboxamide;

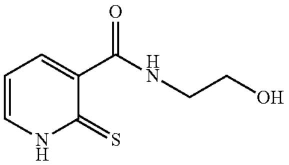 [SMILES: O=C(NCCO)c1ccc[nH]c1=S]

N-(2-hydroxyethyl)-2-thioxo-1,2-dihydropyridine-3-carboxamide;

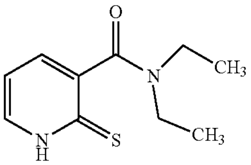

N,N-diethyl 2-mercaptonicotinamide;

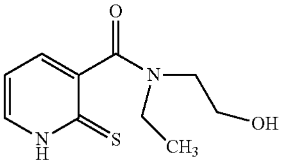

N-ethyl-N-(2-hydroxyethyl)-2-thioxo-1,2-dihydropyridine-3-carboxamide;

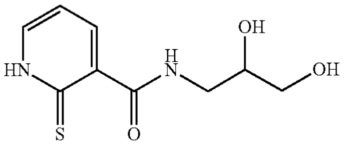 [SMILES: O=C(NCC(O)CO)c1ccc[nH]c1=S]

N-(2,3-dihydroxypropyl)-2-thioxo-1,2-dihydropyridine-3-carboxamide;

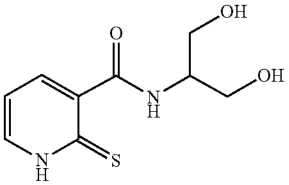 [SMILES: O=C(NC(CO)CO)c1ccc[nH]c1=S]

N-(1,3-dihydroxypropan-2-yl)-2-thioxo-1,2-dihydropyridine-3-carboxamide;

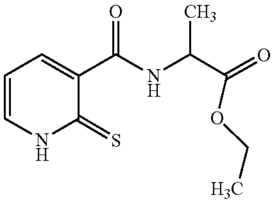 [SMILES: CCOC(=O)C(C)NC(=O)c1ccc[nH]c1=S]

Ethyl N-[(2-thioxo-1,2-dihydropyridin-3-yl)carbonyl]alaninate;

-continued

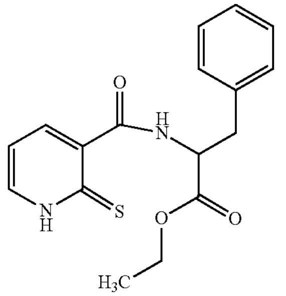 [SMILES: CCOC(=O)C(Cc1ccccc1)NC(=O)c1ccc[nH]c1=S]

Ethyl N-[(2-thioxo-1,2-dihydropyridin-3-yl)carbonyl]phenyl alaninate;

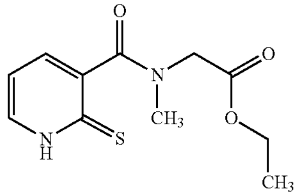

Ethyl N-methyl-N-[(2-thioxo-1,2-dihydropyridin-3-yl)carbonyl]glycinate;

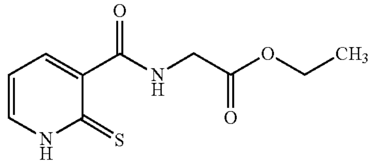 [SMILES: CCOC(=O)CNC(=O)c1ccc[nH]c1=S]

Ethyl N-[(2-thioxo-1,2-dihydropyridin-3-yl)carbonyl]glycinate;

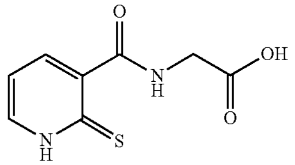 [SMILES: O=C(O)CNC(=O)c1ccc[nH]c1=S]

N-[(2-thioxo-1,2-dihydropyridin-3-yl)carbonyl]glycine;

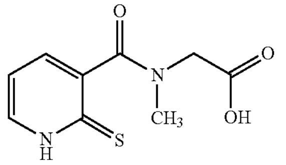

N-methyl-N-[(2-thioxo-1,2-dihydropyridin-3-yl)carbonyl]glycine;

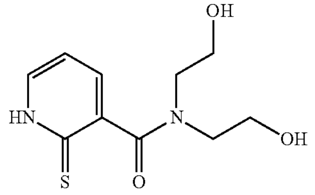

N,N-bis(2-hydroxyethyl)-2-thioxo-1,2-dihydropyridine-3-carboxamide;

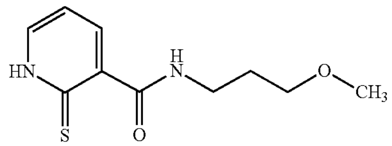

N-(3-methoxypropyl)-2-thioxo-1,2-dihydropyridine-3-carboxamide;

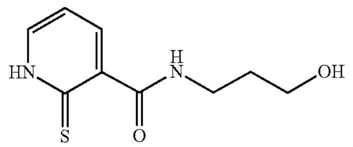 [SMILES: O=C(NCCCO)c1ccc[nH]c1=S]

N-butyl-2-thioxo-1,2-dihydropyridine-3-carboxamide, tautomers thereof, salts thereof, solvates thereof, hydrates thereof, optical isomers thereof, racemates thereof, or mixtures of two or more thereof.

9. The stable composition according to claim 1, wherein the total amount of the i) at least one compound ranges from 0.01% to 10% by weight, relative to the total weight of the composition.

10. The stable composition according to claim 1, wherein, in formula (II):

X represents a heteroatom chosen from oxygen or sulfur;
m is 0 or 1;
$M^{+}$ is a cation; and
R represents a group chosen from:
i) —OH,
ii) —O-$M'^{+}$ with $M'^{+}$ as previously defined for $M^{+}$, or
iii)

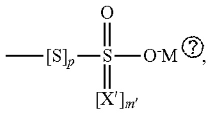

? indicates text missing or illegible when filed wherein:
p is 0 or 2;
m' is 0 or 1;
X' is as defined for X; and
$M''^{+}$ is as previously defined for $M^{+}$,
wherein $M^{+}$, $M'^{+}$, $M''^{+}$ are identical.

11. The stable composition according to claim 1, wherein, in formula (II):

R represents a group chosen from:
i) —OH,
ii) —O-$M'^{+}$ with $M'^{+}$, or
iii)

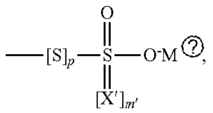

? indicates text missing or illegible when filed wherein:
p is 0 or 2;
m' is 0 or 1;
X' is represents an oxygen atom; and
$M^{+}$, $M'^{+}$, and $M''^{+}$ are independently chosen from sodium or potassium.

12. The stable composition according to claim 1, wherein, in formula (II):

X is sulphur;
m is 1;
$M^{+}$ is sodium or potassium;
R represents a group chosen from:
i) —OH, or
ii) —O-$M'^{+}$ with $M'^{+}$ as previously defined for $M^{+}$, and $M^{+}$, and $M'^{+}$ are identical.

13. The stable composition according to claim 1, wherein the reducing agent is chosen from sodium bisulfite, sodium metabisulfite, sodium sulfite, sodium thiosulfate, sodium sulfate, potassium metabisulfite, potassium sulfite, potassium thiosulfate, potassium sulfate, potassium tetra thionate, or a combination of two or more thereof.

14. The stable composition according to claim 1, wherein the reducing agent is chosen from sodium bisulfite, sodium metabisulfite, sodium sulfite, sodium thiosulfate, sodium sulfate, or a combination of two or more thereof.

15. The stable composition according to claim 1, wherein the total amount of the ii) at least one reducing agent ranges from 0.01% to 2% by weight, relative to the total weight of the composition.

16. The stable composition according to claim 1, wherein arginine is present in an amount ranging from 0.5% to 3% by weight, relative to the total weight of the composition.

17. The stable composition according to claim 1, wherein the composition comprises water in an amount ranging from 20% to 99% by weight, relative to the total weight of the composition.

18. The stable composition according to claim 1, wherein the composition brightens or depigments a keratin material.

19. A cosmetic method of treating a keratin material, the method comprising:

applying the stable composition according to claim 1 on the keratin material.

20. A method of brightening or depigmenting skin, the method comprising:

applying the stable composition according to claim 1 on the skin.

* * * * *